United States Patent [19]

Hui et al.

[11] Patent Number: 5,155,046
[45] Date of Patent: Oct. 13, 1992

[54] SYSTEM AND METHOD FOR MEASURING OXYGEN IN THE PRESENCE OF HALOTHANE

[75] Inventors: Henry K. Hui, Laguna Niguel; Samuel D. Riccitelli, Murrieta; Terry J. Lumsden, San Marcos; George A. Divers, III, San Diego, all of Calif.

[73] Assignee: Puritan-Bennett Corporation, Carlsbad, Calif.

[21] Appl. No.: 565,511

[22] Filed: Aug. 10, 1990

[51] Int. Cl.$^5$ .................. G01N 21/64; G01N 21/77
[52] U.S. Cl. .................. 436/136; 250/458.1; 250/459.1; 422/68.1; 422/56; 422/82.06; 422/82.07; 422/82.08; 436/138; 436/172
[58] Field of Search .................. 422/56–58, 422/68.1, 82.05, 82.08, 82.06, 82.11, 82.07; 436/136, 138, 164, 169, 170, 172; 250/458.1, 459.1, 461.1, 461.2; 128/634; 356/317, 318, 417

[56] References Cited

U.S. PATENT DOCUMENTS

| | | | |
|---|---|---|---|
| 3,725,658 | 4/1973 | Stanley et al. | 436/136 X |
| 4,255,053 | 3/1981 | Lubbers et al. | 356/318 |
| 4,511,660 | 4/1985 | Lubbers et al. | 436/172 X |
| 4,548,907 | 10/1985 | Seitz et al. | 436/163 |
| 4,580,059 | 4/1986 | Wolfbeis et al. | 250/459.1 |
| 4,716,118 | 12/1987 | Wolfbeis et al. | 436/172 X |
| 4,833,091 | 5/1989 | Leader et al. | 436/172 X |
| 4,849,172 | 7/1989 | Yafwo et al. | 436/138 X |
| 4,861,727 | 8/1989 | Hauenstein et al. | 436/136 |
| 4,900,933 | 2/1989 | Nestor et al. | 250/458.1 |
| 5,049,358 | 9/1991 | Lau | 436/169 X |

FOREIGN PATENT DOCUMENTS 0283289  9/1988  European Pat. Off. .
2132348  7/1984  United Kingdom .

OTHER PUBLICATIONS

Wolfbeis et al., "Fiber Optical Fluorosensor for Determination of Halothane and/or Oxygen", Anal. Chem. 1985, 57, pp. 2556–2561.
Gehrich et al., "Optical Fluorescence and Its Application to an Intravascular Blood Gas Monitoring System", Feb. 1986, vol. BME 33, No. 2.
Lee et al., "Luminescence Ratio Indicators for Oxygen", Anal. Chem., 1987, 59, 279–283.

Primary Examiner—Robert J. Hill, Jr.
Attorney, Agent, or Firm—Fulwider, Patton, Lee and Utecht

[57] ABSTRACT

The system for measuring the concentration of oxygen in a fluid sample which may also contain halothane includes a sensor having a matrix containing a first indicator dye which fluoresces at a known wavelength when irradiated with light of a specific wavelength and containing a second indicator dye which fluoresces at a different emission wavelength upon irradiation with light of a similar or different specific wavelength. The fluorescence of the first and second indicator dyes are quenched to a different degree by the presence of oxygen, but the fluorescence of the indicator dyes is quenched to the same degree by halothane. Means are provided for irradiating the indicator dyes in the matrix with the appropriate wavelengths of light, and means are provided for measuring the resultant intensity of fluorescence of the indicator dyes at the different wavelengths of fluorescence. Means are also provided for determining the ratio of the intensity of the different wavelengths of the fluorescence of the indicator dyes, to provide an indication of the concentration of oxygen in the sample measured.

20 Claims, 3 Drawing Sheets

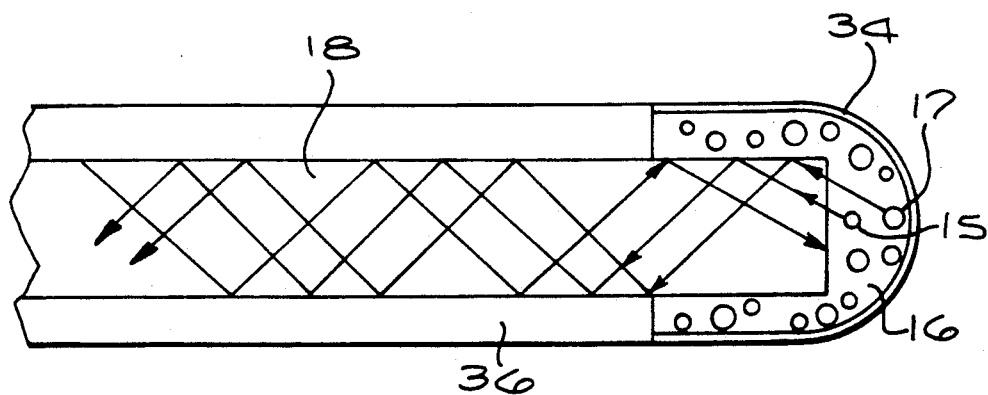
FIG. 3
FIG. 4
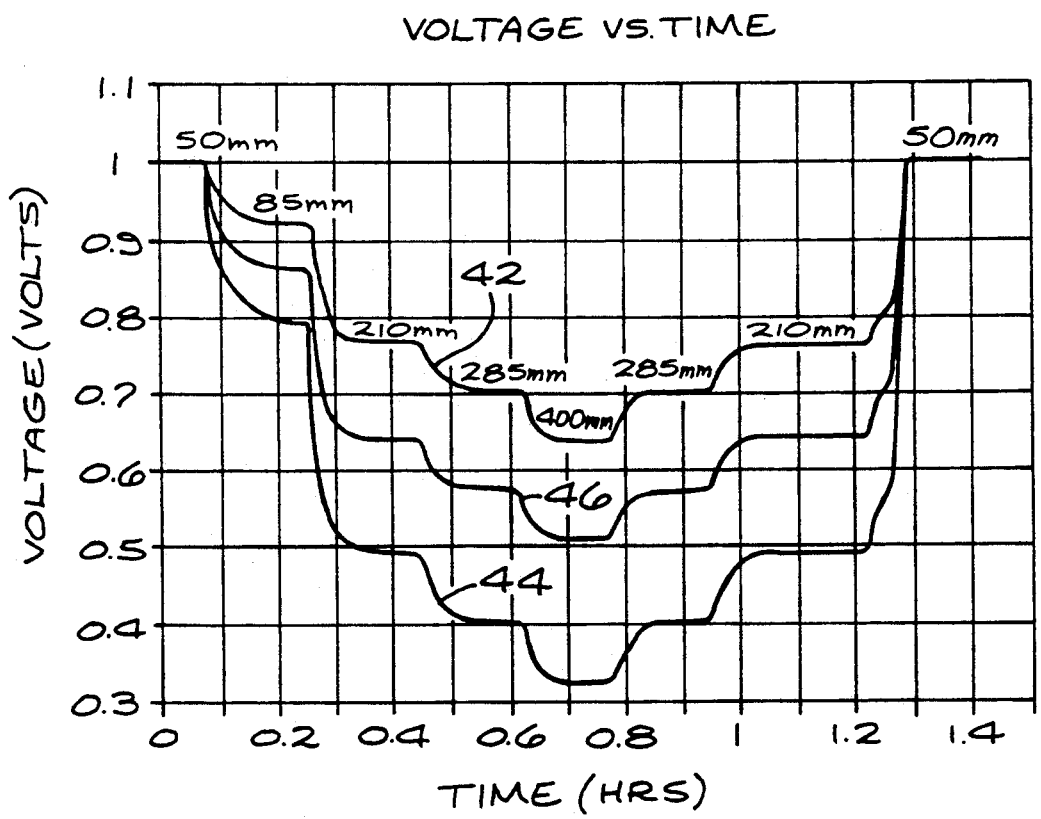

SYSTEM AND METHOD FOR MEASURING OXYGEN IN THE PRESENCE OF HALOTHANE

BACKGROUND OF THE INVENTION

1. Field of the Invention

This invention relates generally to the measurement of the concentration of an analyte in a fluid mixture, and more specifically relates to the measurement of the concentration of oxygen in a fluid sample which may also contain halothane.

2. Description of the Related Art

As life support systems have become more sophisticated, it has become important to provide real time monitoring of critical patient body function parameters. Among the important parameters which should be monitored are those related to blood chemistry, particularly the oxygen, carbon dioxide and pH state of the patient's blood. A variety of techniques to monitor these parameters have been proposed and one particularly promising technique is the use of intravascular sensors which detect the analyte to be measured and transmit a signal proportional to the concentration of the analyte to a remote location. While there are a number of concepts that could be used to perform these functions, such a system can advantageously utilize the phenomena in which the output of certain fluorescent dyes is quenched in proportion to the concentration of an analyte present in a solution to which the dye is exposed. Such concepts have been extensively studied and developed in the context of an optical fiber inserted into the blood vessel and containing at its distal end a quantity of fluorescent dye which is irradiated by light of a first wavelength from a source at the proximal end of the fiber. The emissions from the dye are commonly at a frequency different from that used for excitation and the output of the dye is conducted through the optical fiber from the distal end to a detection means near the proximal end of the fiber. Such a system has been described in the literature and a number of United States patents. One particularly advantageous structure utilizing this phenomenon is that described in Buckles, U.S. Pat. No. 4,321,057, in which the sensor element is distributed along a portion of the optical fiber and the quenching of the signal occurs cumulatively along the length of the sensor element thus deployed. The calibration of such sensors prior to and during their use is a problem not easily addressed, and is particularly difficult if reagents are present which diminish the effectiveness of the sensor material or affect its linearity and sensitivity to the analyte to be measured. A variety of techniques have been proposed to assist in the calibration of the sensor during it's use, but one particularly persistent problem has been the degradation of the sensitivity of such sensors in the presence of halothane such as would be encountered in a patient to whom anesthetic has been administered. Since halothane, a common inhalation narcotic frequently used as an anesthetic during surgery, also quenches the fluorescent effect of oxygen sensitive indicator dyes, this has represented a serious issue for designers of intravascular oxygen sensor systems. Accordingly, it would be advantageous if a means or method could be found to substantially reduce or eliminate the effect of halothane upon the fluorescent indicators used for intravascular sensing of blood oxygen levels.

SUMMARY OF THE INVENTION

The sensing of blood oxygen level in the presence of halothane or other anesthetics represents a serious technical challenge. Since halothane is an anesthetic gas frequently used during the course of surgery and the monitoring of blood oxygen levels during and after surgery is of critical importance to assure the effectiveness of modern life-support systems used to monitor and sustain a person during critical care periods, the present invention provides an improved method and apparatus resulting in a more stable and accurate oxygen sensor for intravascular use with a patient who has been exposed to halothane.

An apparatus according to the invention would include the placement of at least two dyes with differing oxygen sensitivities in a polymer matrix. The two dyes may have similar or different excitation frequencies, but distinctly different emission frequencies. Both dyes are oxygen sensitive, but to a different degree, and the two dyes are chosen to be chemically compatible because of their structural similarity and therefore can be immobilized in the polymer matrix using the same technique. While the dyes are individually oxygen sensitive and also sensitive to the presence of halothane, it has been found that the ratio of the emissions from the two dyes may be used as an indication of oxygen concentration while minimizing the sensitivity to halothane present in the blood.

Briefly, and in general terms, the present invention for measuring oxygen in the presence of halothane includes a sensor having a matrix containing a first indicator dye which fluoresces at a known wavelength when irradiated with light of a specific wavelength and containing a second indicator dye which fluoresces at a different emission wavelength upon irradiation with light of a similar or different specific wavelength to that used to irradiate the first dye. The fluorescence of the first and second indicator dyes are quenched to a different degree by the presence of oxygen, but the fluorescence of the indicator dyes is quenched to a similar degree by halothane. Means are provided for irradiating the indicator dyes in the matrix with the appropriate wavelengths of light, and means are provided for measuring the resultant intensity of fluorescence of the indicator dyes at the different wavelengths of fluorescence. Means are also provided for determining the ratio of the intensity of the different wavelengths of the fluorescence of the indicator dyes, to thereby provide an indication of the concentration of oxygen in the sample measured.

A method of measuring the concentration of an analyte in a mixture containing at least one other component which could activate an indicator would include choosing a plurality of indicators which demonstrated dissimilar sensitivities to the analyte and similar sensitivities to the component contained in the mixture which is not to be measured. The method further includes activating the indicators, measuring the output of the indicators, ratioing the output of the indicators to create a signal representing the relative value of the outputs of the indicators and determining the concentration of the analyte on the basis of a predetermined relationship between the concentration of the analyte and the relative value of the outputs of the indicators when they are simultaneously exposed to a mixture containing a known concentration of the analyte.

Other aspects and advantages of the invention will become apparent from the following detailed description, and the accompanying drawings, which illustrate by way of the example the features of the invention.

BRIEF DESCRIPTION OF THE DRAWINGS

FIG. 3 is a schematic top plan sectional view of the construction of the sensor component of the system;

FIG. 4 is a graph representing the signal outputs and a ratio of the signal outputs of the two indicator dyes at different oxygen concentrations;

DETAILED DESCRIPTION OF THE PREFERRED EMBODIMENT

The present invention is embodied in a system and method which utilizes a single layer of a matrix containing a plurality of indicator dyes which exhibit a fluorescence when exposed to light of a given wavelength which is quenched to different degrees by oxygen, and which is quenched to the same degree by halothane. By measuring the intensity of fluorescence over at least two different specific wavelength ranges which are affected by the different oxygen quenching sensitivities of the indicator dyes, and by determining a ratio of the intensities of fluorescence of the indicator dyes, a normalized measurement of fluorescence quenching due to the presence of oxygen may be measured without the need for separating the dye indicators, and without the need for complicated calculations. While the invention is amenable to various combinations of indicators, it has been found that an effective and accurate measurement of oxygen in blood in the presence of halothane may be made using two such fluorescent dyes.

Figure 1:
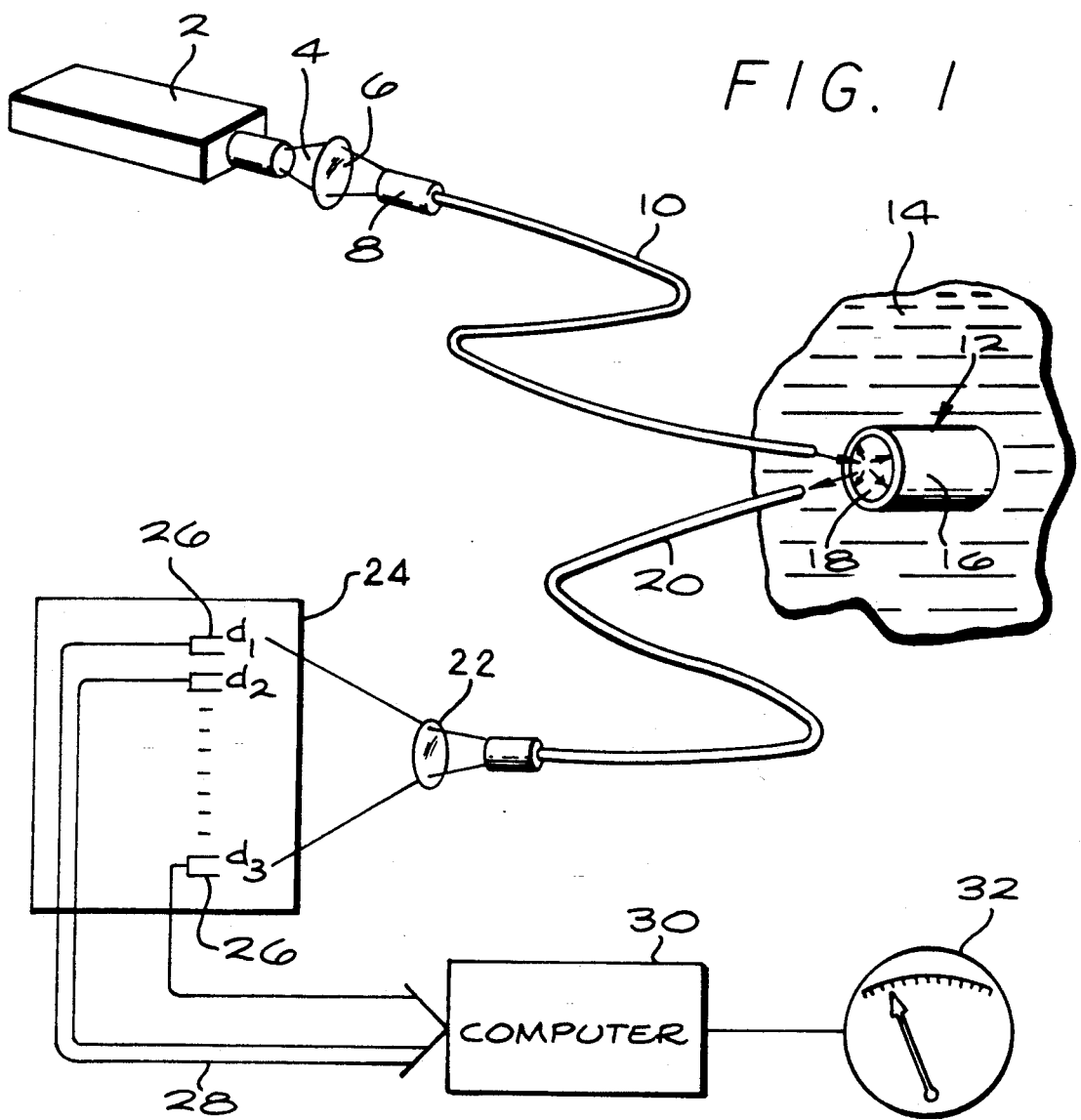
FIG. 1 is a schematic diagram of the system of the invention.
Figure 2:
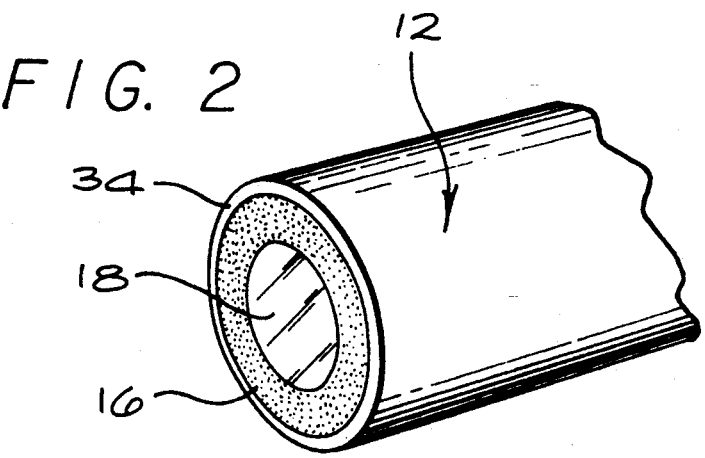
FIG. 2 is an enlarged cross-sectional perspective view of the sensor component of the system.

Referring now to the drawings, and particularly to FIG. 1, a light source 2 provides an output light beam 4 that is focused by a lens system 6 into a connector 8 of an optical fiber 10, which carries the light beam to a sensor module 12 at a distal end of the optical fiber. The light source preferably includes an excitation filter for controlling the wavelength range of the light provided to the sensor module. Sensor module 12 is adapted to be placed in a fluid 14, such as blood, having a concentration of oxygen to be measured. Since halothane may be contained in inhalation gases used during anesthesia of patients undergoing surgery, the fluid may also contain a concentration of halothane. The sensor module 12 incorporates a first dye material 15 and a second dye material in a polymeric matrix 16, which is typically silicone, and more specifically may be polydimethylsiloxane. As is illustrated in FIG. 2, the matrix material immobilizing the dye indicators generally surrounds the optical fiber material 18. An output optical fiber 20 is also connected to the sensor module to carry light fluoresced from the indicator dyes in the matrix material to a lens system 22, which focuses the fluoresced light from the indicator dyes upon a detector array 24 containing two or more detectors 26, each of which is sensitive to various output wavelengths of light to be measured. In practice, the detectors may be identical and fitted with filters in order to measure the intensity of fluorescence from each particular indicator dye in response to the excitation light. Also, while separate optical fibers have been illustrated for the excitation and output light paths, those skilled in the art will recognize that, in practice, a single optical fiber may be used for both light paths, thus simplifying the apparatus. The electrical output of the detectors is fed through cables 28 to a computer 30 which receives the electrical output of the detectors and determines the percentage of the oxygen analyte present in the fluid sample on the basis of the ratio of the fluorescence intensity signals detected by the individual detectors. As discussed below, the calculation of oxygen concentration is based upon the relationship between the degree of quenching due to the presence of oxygen in the sample for two or more dyes exposed to the sample. In practice, the calculations performed by the computer may either be based upon the empirical measurement of the output of the indicators when exposed to representative concentrations of the analyte and contaminant or upon mathematical or algorithmic representations of the phenomena observed or calculated from such relationships. In either event, the calculations are well within the capabilities of a relatively small computer adaptable to instrumentation of the type used with blood chemistry monitoring systems. The output of the computer may be provided in the form of a meter 32 or other means to provide a direct indication of the concentration of oxygen in the sample.

Referring to FIGS. 2 and 3, the light conducting material 18 transmits light from the light source to the indicator dye materials 15 and 17 immobilized in the matrix 16 around the light conducting material. Appropriate systems for use in the sensor probe include the use of dye indicators such as coronene and decacyclene, chemically incorporated into the silicone matrix, such as a cross-linked polydimethylsiloxane matrix surrounding the light conductor material. Polydimethylsiloxane and cross-linked derivatives and copolymers thereof may also be suitable choices for forming the matrix. An oxygen permeable membrane 34 covers the matrix extending distally beyond the cladding 36 of the optical fiber, to exclude unwanted large molecules, while allowing the mixing of the oxygen with the dye indicators to permit quenching of the fluorescence reaction of the dye indicators by oxygen from the fluid sample.

Coronene is preferably used as the first dye indicator and decacyclene is preferably used as the second dye indicator in the silicone matrix. These two dyes are chemically compatible because of their structural similarity, so they can both be immobilized in the same polymer matrix with the same technique. These dyes were selected as exemplary indicator dyes because they are oxygen sensitive to a different degree, and halothane sensitive to the same degree. Other dyes having similar characteristics may also be used, and can have similar or different excitation frequencies, but preferably should have distinctly different emission frequencies. The coronene and decacyclene dye indicators are both preferably excited at $366 \pm 20$ nm, and the fluorescence emissions from these two dye indicators are collected at approximately $430 \pm 20$ nm and approximately $520 \pm 25$ nm, corresponding to the fluorescence wavelengths of coronene and decacyclene, respectively. Alternatively, coronene may be excited at approximately 366±25 nm, and decacyclene may be excited with light of approximately 420±20 nm. The fluorescence of decacyclene may then also be monitored at 480±20 nm. In either case, the intensity of the fluorescence at the different wavelengths ranges is measured by the detectors, and the fluorescence emission signals are utilized by the computer to determine a ratio of the fluorescence intensities. The fluorescence intensities may be used to determine the fluorescence intensity of each dye indicator substance in the absence of oxygen ($F_0$) and the Stern-Volmer constants may be determined from fluorescence intensity measurements taken from two or more fluid samples having different oxygen concentrations. After calibration, the fluorescence intensity ratios may be used to provide a direct indication of the concentration of oxygen in the sample, without regard to the concentration of halothane in the fluid sample. Generally it has been found that the system of the invention is accurate in determining oxygen concentrations and unaffected by interference by halothane quenching up to a concentration of approximately 3% halothane.

As is illustrated in FIG. 4, the fluorescence intensity signal outputs of coronene and decacyclene at different oxygen partial pressures may be used to determine a ratio of the fluorescence intensity signals which has been found to be a reliable indicator of oxygen partial pressures. In the figure, the upper line 42 represents the fluorescence intensity of decacyclene at different oxygen levels, and the lower line 44 traces the signal output of coronene at the same oxygen levels. The ratio of the two emission signals is indicated by the middle line 46. The advantage of the ratio signal represented by the middle line is that this parameter is relatively insensitive to the presence of halothane, since both dye indicators are sensitive to quenching of the fluorescence reaction by halothane to the same degree.

Figure 5:
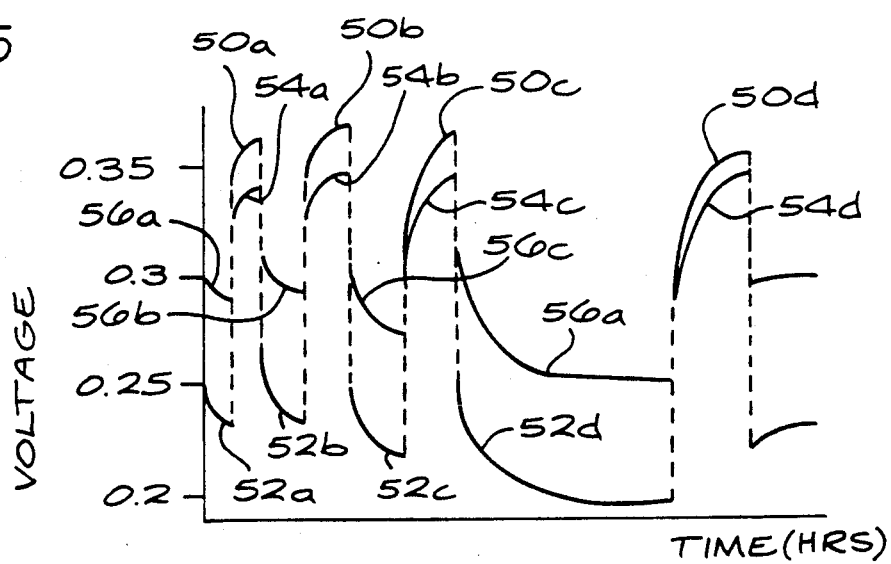
FIG. 5 is a graph representing the fluorescence signal outputs of coronene and decacyclene at different halothane levels in air.
Figure 6:
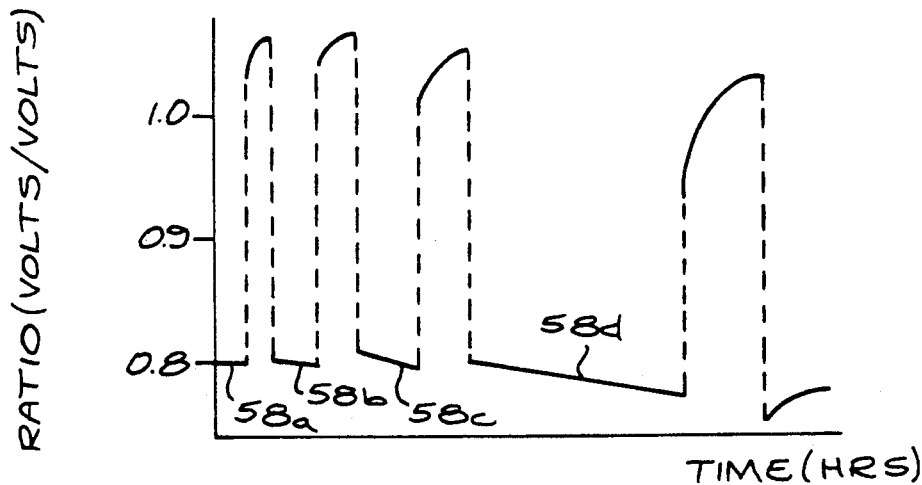
FIG. 6 is a graph representing the ratio of the signal outputs of FIG. 5.
Figure 7:
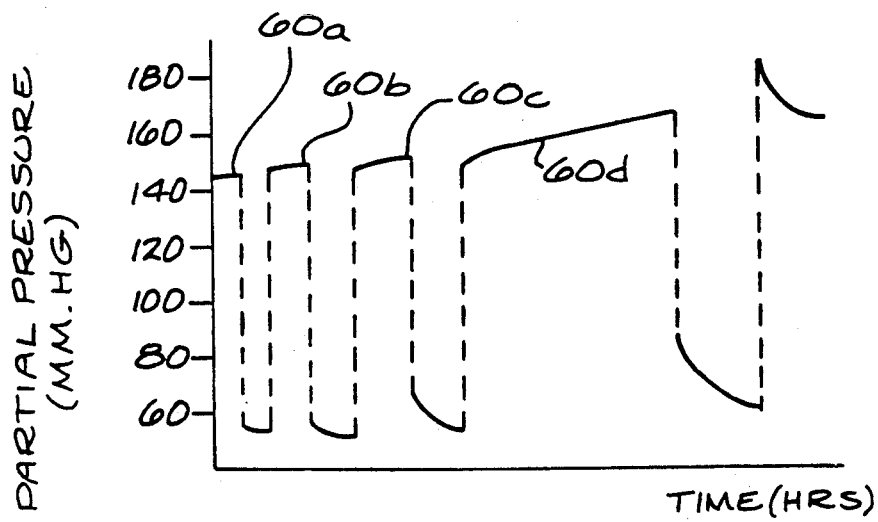
FIG. 7 is a graph representing the effect of different halothane levels on the partial pressure of oxygen measured with the system of the invention.

The graphs shown in FIGS. 5-7 further illustrate how the ratio of the fluorescence signals may be used to provide a reliable indication of oxygen partial pressure which is relatively insensitive to the presence of halothane. In FIG. 5, the lines 50*a, b, c, d* and 52*a, b, c, d* represent the fluorescence signal of coronene; and lines 54*a, b, c, d* and 56*a, b, c, d* represent the fluorescence signal of decacyclene, at various concentrations of halothane in air over time. Lines 50*a-d* show calibration levels of coronene, and lines 52*a-d* show coronene fluorescence intensity signal at gas sample concentrations of 0.5%, 1%, 3% and 5% halothane in air, respectively. As the coronene signal measurements leveled off, the probe was recalibrated with a standardized gas mixture, before changing the halothane gas sample mixture. Similarly, lines 54 *a-d* show the calibration levels of decacyclene, and lines 56*a-d* show the decacyclene fluorescence intensity signal at gas sample concentrations of 0.5%, 1%, 3% and 5% halothane in air, respectively. It can be seen that coronene is more sensitive to fluctuations in the concentration of oxygen, but that the fluorescence intensity of coronene and decacyclene are affected to a similar degree by the presence of halothane.

In FIG. 6, it can be seen that the ratio of the fluorescence intensity signal from coronene taken from FIG. 5, divided by the signal from decacyclene, taken from FIG. 5, is relatively stable over the range of gas sample concentrations of 0.5%, 1%, 3% and 5% halothane in air, respectively, at lines 58*a-d*. The partial pressures of oxygen (in millimeters Hg), corresponding to the ratios of FIG. 6, are shown in the graph of FIG. 7. It can be seen that the lines 60*a-d* corresponding to gas sample concentrations of 0.5%, 1%, 3%, and 5% halothane in air are relatively stable, partial pressure representing oxygen measurements ranging from about 150 mm. Hg to about 165 mm. Hg.

It should be recognized that various other structural details and method steps may be used in the practice of the invention described herein. For example, while the apparatus is illustrated in the form of individual optical fibers for the respective irradiation and collection of data from the sensor module, those skilled in the art will appreciate that other methods, including time multiplexing and beam splitting, may be used to simplify or alter this apparatus for certain applications.

It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. A method of measuring a concentration of an analyte to be measured in a solution which also contains a contaminant comprising:

choosing a plurality of indicators having outputs which are individually sensitive to said analyte and to said contaminant but wherein a ratio of said outputs is sensitive to the analyte to be measured and is insensitive to the contaminant, and having sufficient chemical compatibility to allow the immobilization of both dyes in a common polymer matrix;

exposing to the solution a matrix into which the indicators have been immobilized;

activating the indicators;

measuring the output of the indicators;

deriving a signal representing the ratio of the outputs of the indicators; and determining the concentration of said analyte in said solution based upon predetermined relationships between said ratio and the concentration of said analyte in a solution.

2. The method of claim 1 wherein said indicators are fluorescent indicators which emit a signal at a frequency different from that used to activate them.

3. The method of claim 2 wherein said analyte is oxygen and said contaminant is halothane.

4. The method of claim 2 wherein said indicators include coronene and decacyclene.

5. The method of claim 4 wherein said matrix is a permeable silicone membrane material selected from the group consisting of polydimethylsiloxane, cross-linked polydimethylsiloxane, and cross-linked derivatives and copolymers thereof.

6. The method of claim 1 wherein the step of determining the concentration of said analyte in said solution based upon predetermined relationships between said ratio and the concentration of an analyte in a solution includes the step of exposing the indicators to solutions containing various concentrations of the analyte and contaminant in the concentration ranges of interest and measuring the outputs therefrom.

7. An apparatus for the measurement of the concentration of an analyte in a solution containing a contaminant comprising:

sensor means, including a plurality of indicators in a common polymeric matrix, said indicators having a ratio of their outputs which is altered by the presence of said analyte, said ratio of said outputs of said indicators further being relatively insensitive to the presence of said contaminant;
means to activate said indicators;
means to measure the outputs of said indicators;
means to determine the ratio of the output of said indicators; and
means to derive from said ratio of the output of said indicators the concentration of the analyte to be measured.

8. The apparatus of claim 7 wherein said indicators are fluorescent indicators whose output is quenched in the presence of the analyte to be measured.

9. The apparatus of claim 8 wherein the outputs of said indicators are in frequency spectra different from one another.

10. The apparatus of claim 9 in which one of said indicators is coronene.

11. The apparatus of claim 9 in which one of said indicators is decacyclene.

12. The apparatus of claim 8 wherein said matrix comprises a permeable silicone membrane material selected from the group consisting of polydimethylsiloxane, cross-linked polydimethylsiloxane, and cross-linked derivatives and copolymers thereof.

13. The apparatus of claim 7 in which said analyte is oxygen and said contaminant is halothane.

14. A system for measuring the concentration of oxygen in the presence of halothane in a fluid sample to be measured, which comprises:
sensor means having a permeable matrix adapted to be exposed to said sample, said matrix containing a first indicator material which exhibits fluorescence at a first emission wavelength when exposed to a first energy of excitation, said matrix containing a second indicator material which exhibits fluorescence at a second emission wavelength different from said first emission wavelength when exposed to a second energy of excitation, a ratio of said fluorescence of said first indicator material and said second indicator material being sensitive to quenching by oxygen, and said ratio being relatively insensitive to quenching by said halothane;
means for providing said first indicator material and said second indicator material with said first and second energies of excitation;
means for measuring intensity of said fluorescence at said first and second emission wavelengths; and
means for determining said ratio of intensity of said fluorescence of said first and second indicator materials at said first and second emission wavelengths to determine an indication of the concentration of oxygen in said sample.

15. The system of claim 14, wherein said first indicator material is coronene.

16. The system of claim 14, wherein said indicator material is decacyclene.

17. The system of claim 14, wherein said matrix comprises a permeable silicone membrane material selected from the group consisting of polydimethylsiloxane, cross-linked polydimethylsiloxane and cross-linked derivatives and copolymers thereof.

18. A method for measuring the concentration of oxygen in the presence of a halothane in a fluid sample to be measured, which comprises the steps of:
providing a first energy of excitation to a first indicator material which exhibits fluorescence at a first emission wavelength when exposed to said first energy of excitation;
providing a second energy of excitation to a second indicator material which exhibits fluorescence at a second emission wavelength different from said first emission wavelength when exposed to said second energy of excitation, a ratio of said fluorescence of said first indicator substance and said second indicator substance being sensitive to quenching by oxygen, and said ratio being relatively insensitive to quenching by said halothane;
measuring said fluorescence at said first and second wavelengths; and
determining said ratio of said fluorescence at said first and second emission wavelengths to determine an indication of the concentration of oxygen in said fluid sample.

19. The method of claim 18, wherein said first indicator material is coronene.

20. The method of claim 18, wherein said second indicator material is decacyclene.

* * * * *